United States Patent [19]

Hägele et al.

[11] Patent Number: 5,309,591
[45] Date of Patent: May 10, 1994

[54] ELECTRIC TOOTHBRUSH WITH PUSH-ON PROTECTIVE COVER

[75] Inventors: Walter Hägele, Frankfurt/M.; Peter Hartwein, Königstein/Ts., both of Fed. Rep. of Germany

[73] Assignee: Braun Aktiengesellschaft, Frankfurt, Fed. Rep. of Germany

[21] Appl. No.: 4,467

[22] Filed: Jan. 14, 1993

[30] Foreign Application Priority Data

Jan. 17, 1992 [DE] Fed. Rep. of Germany ....... 4201091

[51] Int. Cl.⁵ ............................................. A46B 17/04
[52] U.S. Cl. ......................................... 15/22.1; 15/23; 15/184; 15/247
[58] Field of Search ...................... 15/22.1, 22.2, 22.4, 15/23, 24, 28, 29, 184, 247, 97.1; 310/50, 85, 89; 132/119.1, 73.6, 75.8; 128/62 A

[56] References Cited

U.S. PATENT DOCUMENTS

| | | |
|---|---|---|
| 4,189,801 | 2/1980 | Lanusse ................ 15/22.1 |
| 4,344,202 | 8/1982 | Hayat .................... 15/22.1 |
| 4,845,796 | 7/1989 | Mosley .................. 15/23 |
| 4,924,849 | 5/1990 | Zaborowski . | |

FOREIGN PATENT DOCUMENTS 2174896 11/1986 United Kingdom .

Primary Examiner—Edward L. Roberts
Attorney, Agent, or Firm—Fish & Richardson

[57] ABSTRACT

The invention is directed to an electric toothbrush provided with a protective cover which is adapted to be pushed onto the handle section of the toothbrush. The protective cover protects in particular the drive shaft of the toothbrush extending from the handle section from contaminants, liquids as well as the impact of forces. The protective cover is further provided with a safety interlock preventing an accidental operation of the electric toothbrush when the protective cover is seated in place. A notch already provided is used for accomplishing a firm locking engagement of the protective cover with the handle section. The embodiments described cover both an integral and a two-part structure of the protective cover.

19 Claims, 9 Drawing Sheets

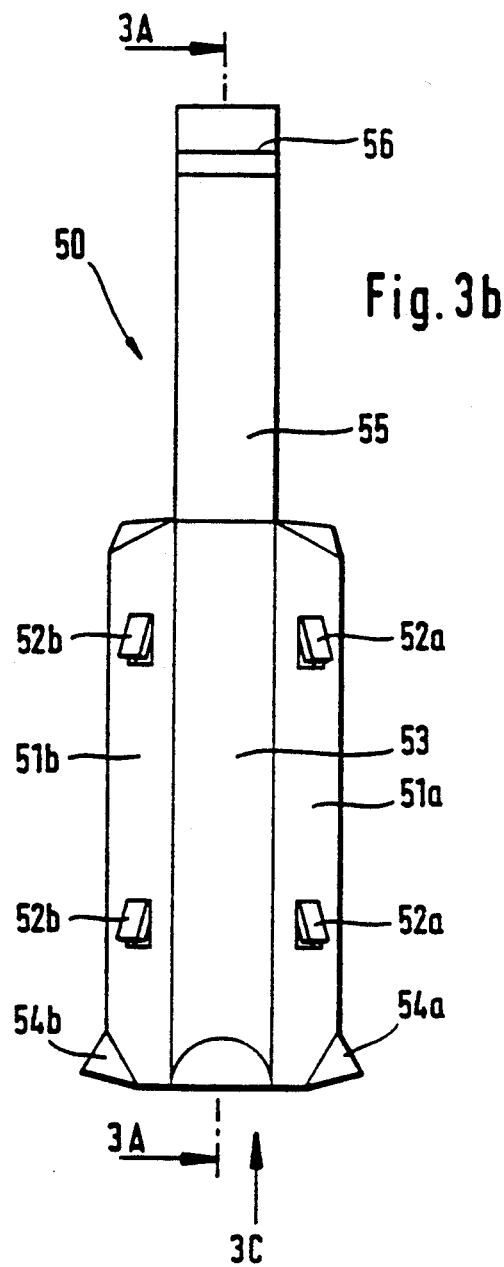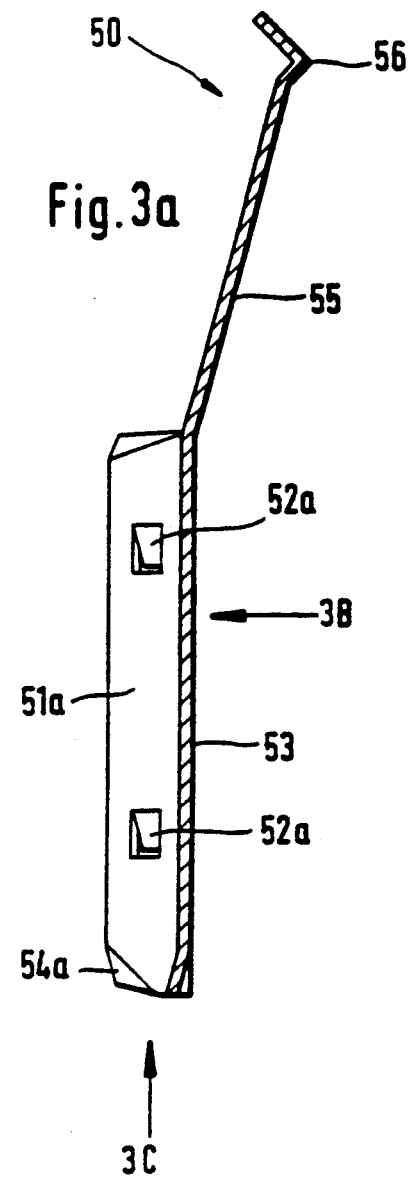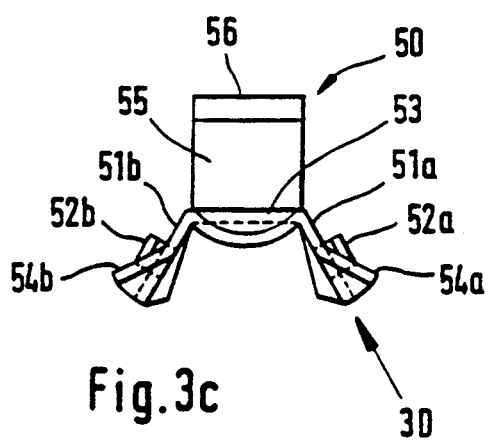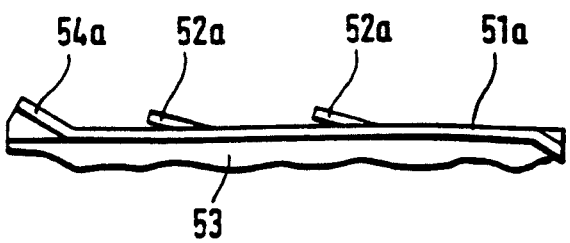

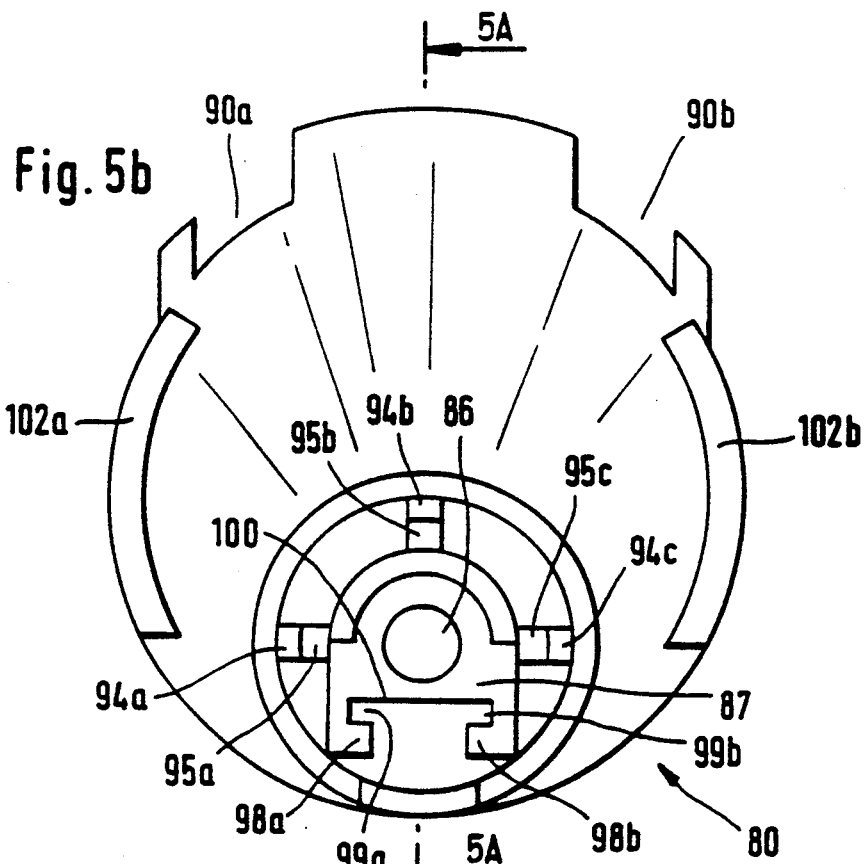
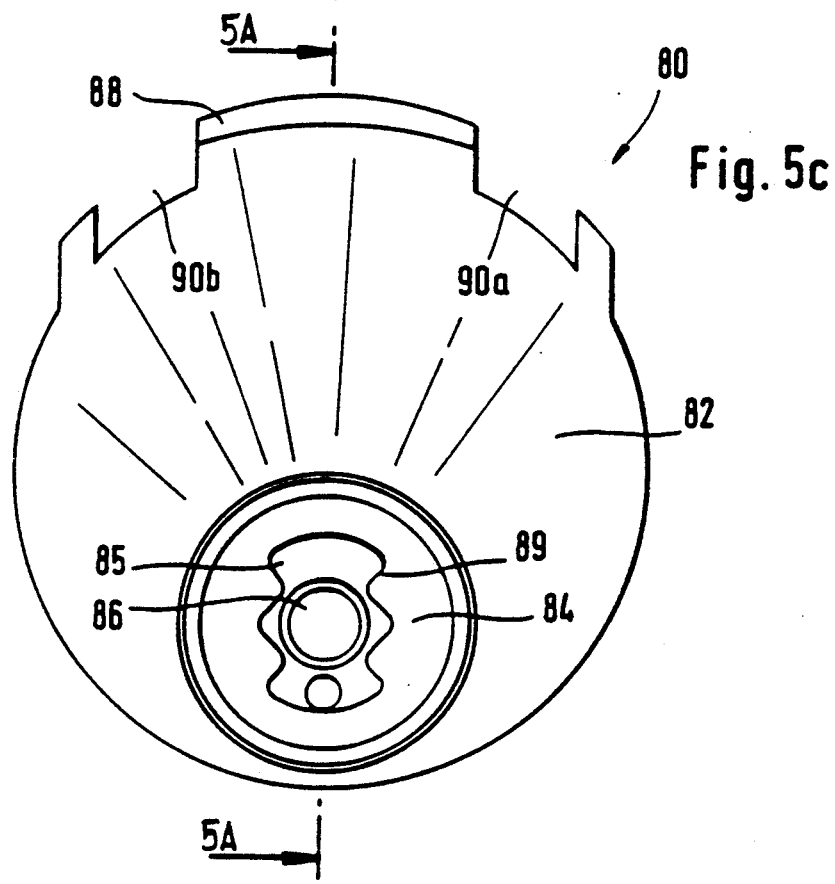

ELECTRIC TOOTHBRUSH WITH PUSH-ON PROTECTIVE COVER

This invention relates to a protective device for an electric toothbrush including a handle section accommodating an electric motor drive mechanism as well as a switch providing at least two switch positions reflecting an On and an Off condition of the electric motor drive mechanism.

An electric toothbrush of this type is known, for example, from U.S. patent application Ser. No. 07/855,707, filed May 5, 1992 and assigned to Braun AG. In this application, an electric toothbrush is described which is comprised of a handle section and a brush section detachable therefrom. The handle section receives an electric motor drive mechanism with associated accumulators and an On/Off switch. To mount the brush section, a drive shaft which is connected with the electric motor drive mechanism projects from a housing shank of the handle section. To radially secure the brush section to the handle section, the housing shank is provided with a specific cross-sectional profile. For axially securing the brush section to the drive shaft, the drive shaft is provided with a notch for locking engagement with a lug of the brush section when pushed on. The driving torques are transmitted to the brush section by having one side of the drive shaft flattened. Such or similar toothbrushes may be stored in travel cases while in transit. Such cases are, however, relatively large and awkward to handle.

When it is desired to transport such an electric toothbrush without such a case, as when a user wishes to take the toothbrush along on a trip and pack it in the luggage, it is advisable to detach the brush section from the handle section, because otherwise a high leverage may act on the drive shaft and damage it. However, with the brush section removed, the drive shaft is completely exposed, projecting from the handle section, in which case the drive shaft may damage, for example, nearby clothes in the user's luggage.

Further, with the brush section removed, the drive shaft and in particular the seal of the drive shaft in the housing shank are completely freely exposed to all kinds of environmental effects as, for example, dirt, dust and liquids. Finally, when the electric toothbrush is carried along in a user's luggage, there is the permanent risk that the electric toothbrush turns on accidentally by altering its position and the like, accordingly operating while in transit. This may deep-drain the accumulators supplying energy to the electric motor drive mechanism, which may damage or even destroy the accumulators, at all events it may result in lack of serviceability of the toothbrush.

It is an object of the present invention to improve upon a protective device for an electric toothbrush of the type initially referred to in such a manner as to ensure a safe transport of the toothbrush with the brush section removed and afford ease of handling and stowage of the protected toothbrush.

In a protective device for an electric toothbrush of the aforementioned type, this object is accomplished by the invention in that a protective cover is provided which is adapted to be pushed on the handle section and includes a safety interlock configured such that, with the protective cover pushed on, the switch is prevented from going from the Off position to the On position.

The protective cover, when pushed on, prevents the impact of any forces on the drive shaft. The protective cover further protects the drive shaft from entry of contaminants or liquids. This thus eliminates the risk for the drive shaft to be damaged by external action, in particular by external forces. Still further, the risk of any damage caused by the drive shaft is eliminated, because the protective cover, in surrounding the drive shaft, prevents this from occurring. Moreover, the safety interlock provided on the protective cover prevents accidental operation of the electric toothbrush with the protective cover pushed on. This prevents the possibility of deep discharges and thus damage of the accumulators when the protective cover is seated in place. The protective cover thus allows an, in all respects, safe transport of the electric toothbrush.

In a feature of the present invention, the handle section and the protective cover are of a barrel-shaped configuration. The switch of the toothbrush is actuatable in the longitudinal direction, with the switch position reflecting the Off condition being provided at the end remote from the protective cover when viewed in the longitudinal direction. In this feature, with the protective cover seated in place, the safety interlock extends in the longitudinal direction beyond the boundaries of the protective cover, reaching up to the switch of the toothbrush. The switch is then in the position reflecting the Off condition. To activate the electric motor drive mechanism, it would be necessary to move the switch in the longitudinal direction towards the protective cover. This is, however, prevented from occurring by the safety interlock abutting the switch with the protective cover pushed on. Accordingly, with the protective cover pushed on, the switch can not be moved to the On position. This thus prevents the electric motor drive mechanism from being operated accidentally when the protective cover is in pushed-on condition.

In a further feature of the present invention, the protective cover includes locking means serving to axially locate the protective cover on the drive shaft of the handle section. In this arrangement, the locking means become operatively associated with a notch on the drive shaft, such as to retain the protective cover in pushed-on condition. By virtue of this locking engagement between the protective cover and the drive shaft of the handle section, the protective cover cannot become disengaged readily, that is, an accidental removal of the protective cover from the handle section is not readily possible. It will be understood that this location of the protective cover on the drive shaft of the handle section is independent of the safety interlock and the attendant features of the protective cover, that is, a protective cover may be provided which, while including such a location, has no safety interlock. In this feature it is particularly advantageous if the notch in the drive shaft serves at the same time a locating function for a brush section on the handle section. In this event, the notch serves to secure several components axially, including the brush section during operation of the toothbrush on the one hand and, on the other hand, the protective cover while the toothbrush is in transit.

In an advantageous embodiment of the present invention, the protective cover is an integral structure. It includes recesses for receiving the drive shaft and the housing shank from which the drive shaft projects. In this arrangement, the recesses have at least in part a cross-sectional profile complementary to the cross-sectional profile of the housing shank. The protective cover is thereby radially secured to and located on the housing shank. The position of the protective cover relative to the handle section is clearly defined by the complementary cross-sectional profiles. The protective cover further has two grooves extending parallel to the recesses and serving to receive a detent spring. The detent spring possesses means guiding it within the grooves of the protective cover and preventing it from falling out of the protective cover. The detent spring further includes a locking tab falling into the notch of the drive shaft with the detent spring inserted and the protective cover pushed on. In this manner, a locking engagement is accomplished between the protective cover and the drive shaft of the toothbrush.

In another advantageous embodiment of the present invention, the protective cover is comprised of an outer portion and an inner portion. Both portions are provided with relatively cooperating means which in assembled condition of the protective cover firmly connect the two portions with each other, preventing them from disengagement. The inner portion of this protective cover includes recesses for receiving the drive shaft and the housing shank from which the drive shaft projects. The recesses have at least in part a cross-sectional profile complementary to the cross-sectional profile of the housing shank. This results in a radial location of the protective cover on the housing shank. The position of the protective cover relative to the handle section is thereby clearly defined. The inner portion further has two grooves extending parallel to the recesses and serving to receive a detent spring. The detent spring possesses means preventing it from falling out, and it further includes a locking tab falling into the notch of the drive shaft with the detent spring inserted and the protective cover assembled and pushed on. In this manner, the protective cover is axially located on the drive shaft. Owing to the locking engagement between the protective cover and the drive shaft, a secure location of the protective cover on the handle section is ensured.

The two-part configuration of the protective cover makes it possible to provide the inner portion with a guided-entry surface along which the drive shaft may slide when the protective cover is pushed onto the handle section, thereby facilitating the push-on procedure materially.

In all features and embodiments of the present invention, it is advantageous to configure the protective cover in cup shape such that it surrounds the drive shaft of the handle section as completely as possible, thereby affording optimum protection. Further it is advantageous to manufacture the protective cover as an injection-molded plastic part, enabling the protective cover to be matched with the toothbrush in a simple manner in respect of form, material, and color.

It will be appreciated that the present invention is suitable for implementation not only in the form of a toothbrush comprised of a handle section and an associated protective cover, but also in the form of a protective cover provided for and adapted to an already existing handle section.

Further advantages of the present invention will become apparent from the subsequent description of two embodiments of the protective cover of the invention adapted to be pushed on an electric toothbrush, reference being had to the accompanying drawings. In particular, it will be understood that the protective cover per se constitutes the subject-matter of the present invention, independent of its employment with an electric toothbrush.

FIGS. 3a to 3d are various representations of a detent spring for the integrally formed protective cover of FIGS. 2a and 2b;

Figure 4A:
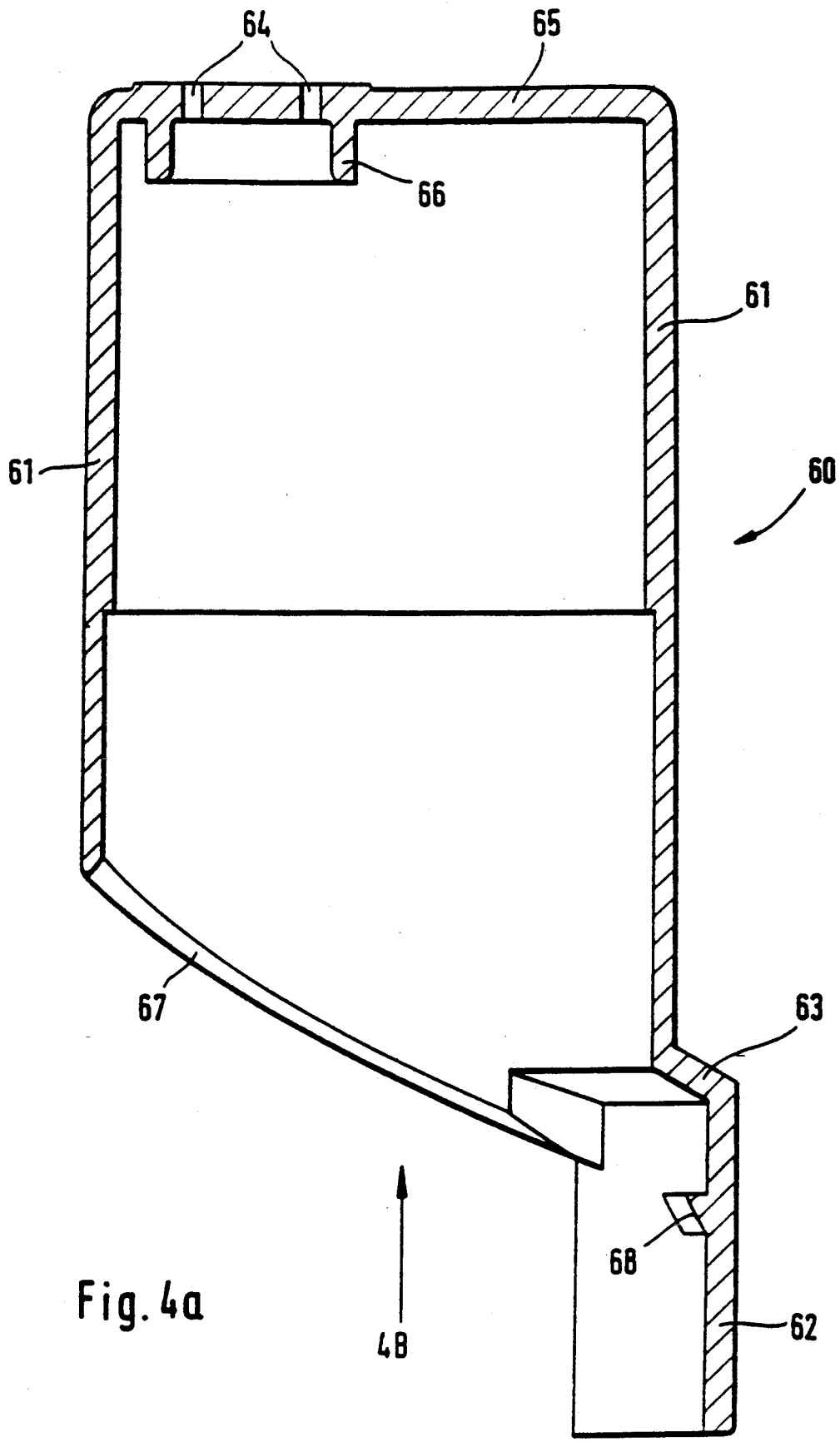
FIGS. 4a and 4b are, respectively, a sectional view of an outer portion of a two-part protective cover and a view into the interior of the protective cover.
Figure 4B:
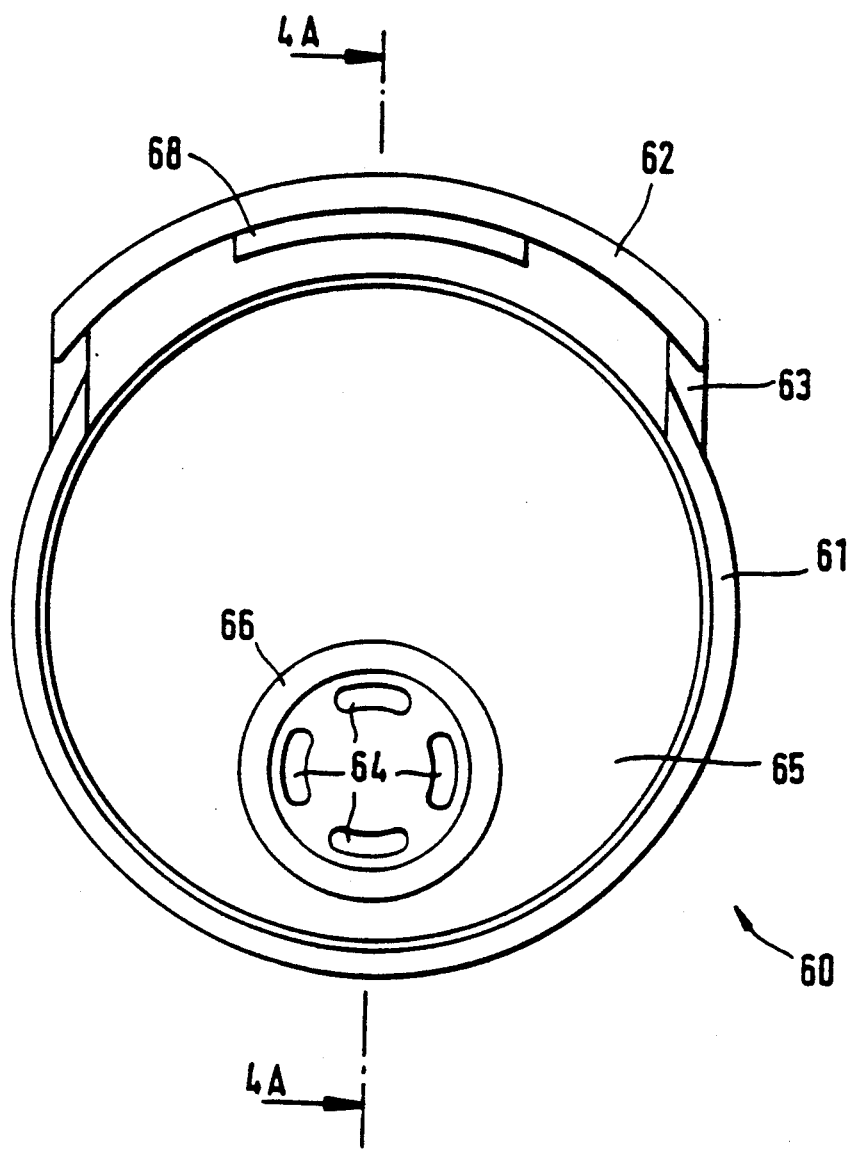
Figure 5A:
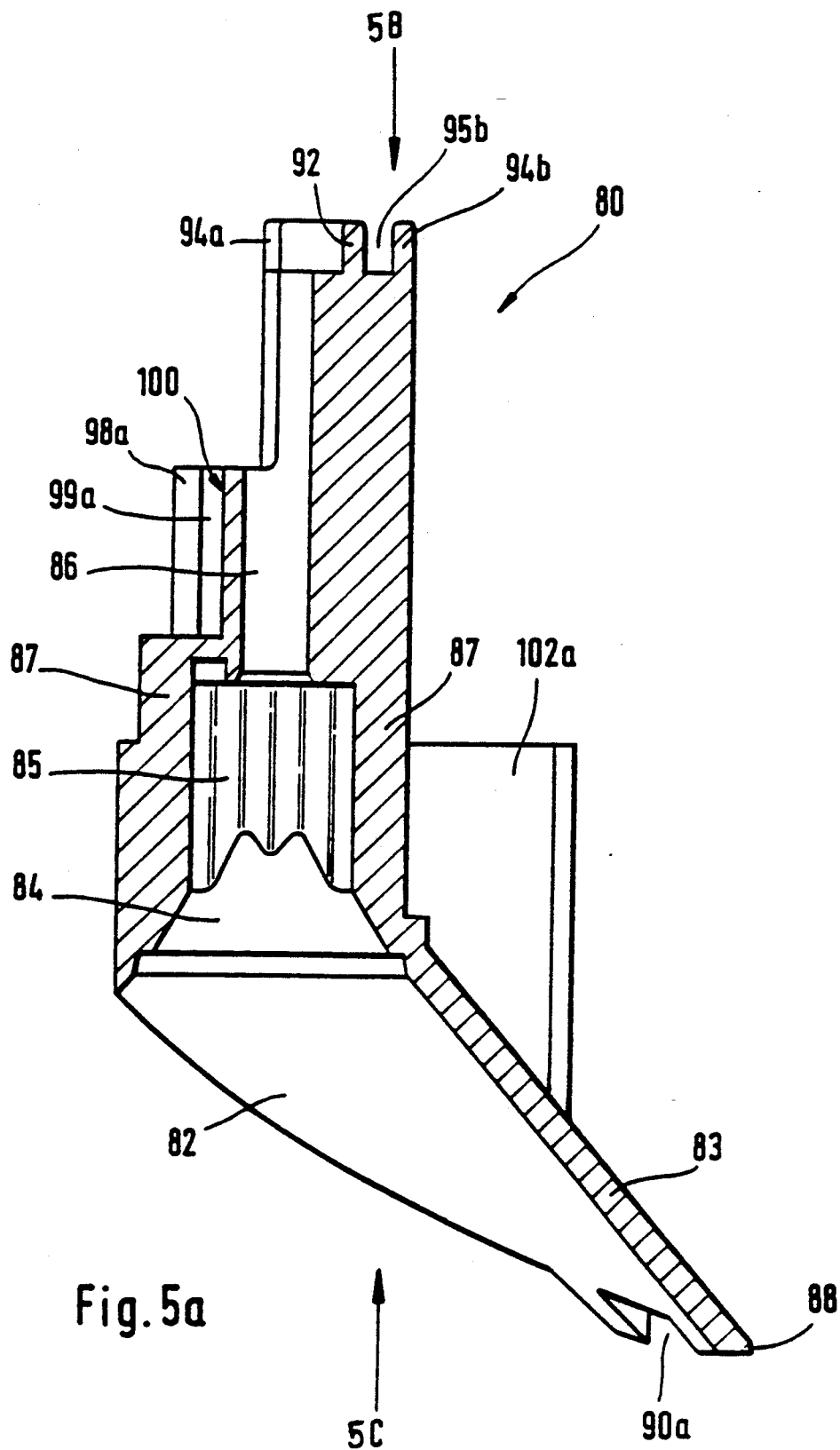
Figure 5D:
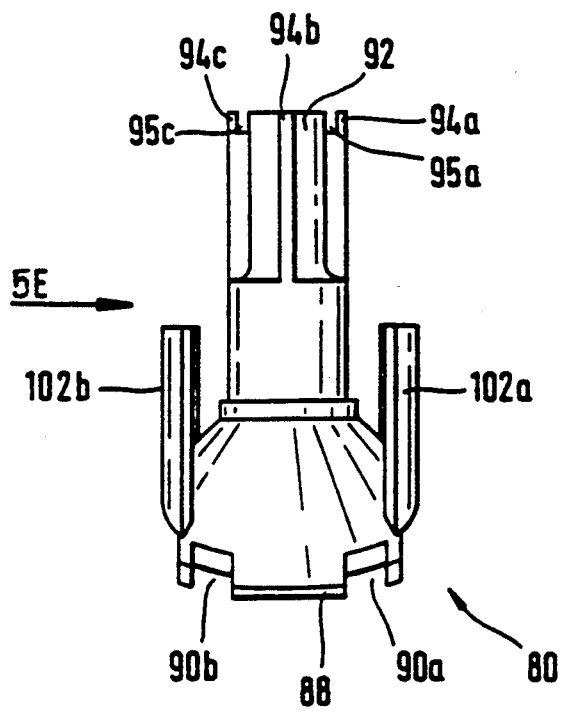
Figure 5E:
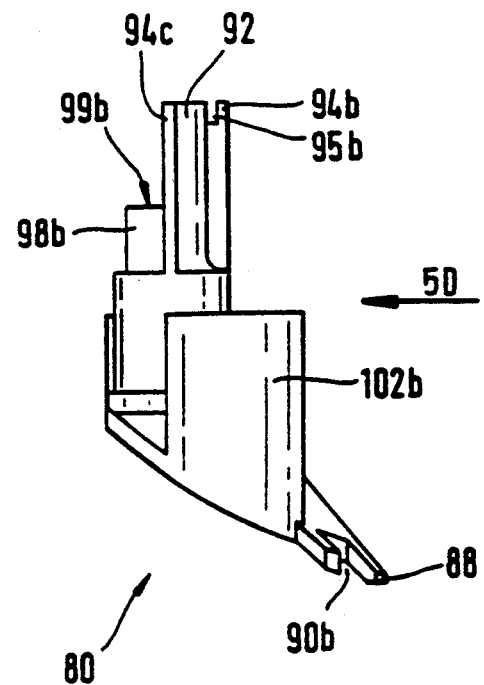
Figure 6A:
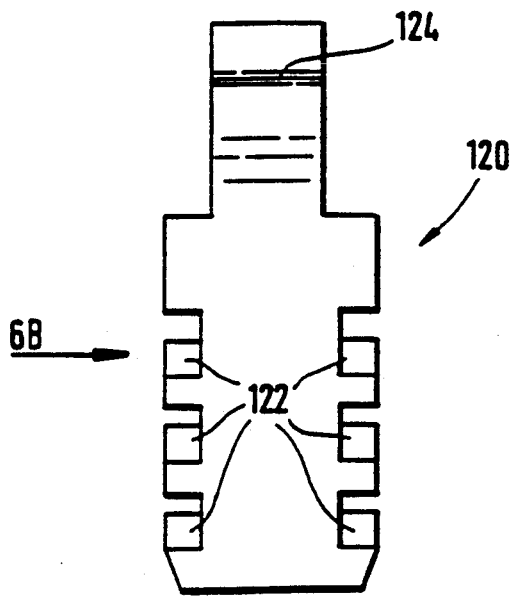
Figure 6B:
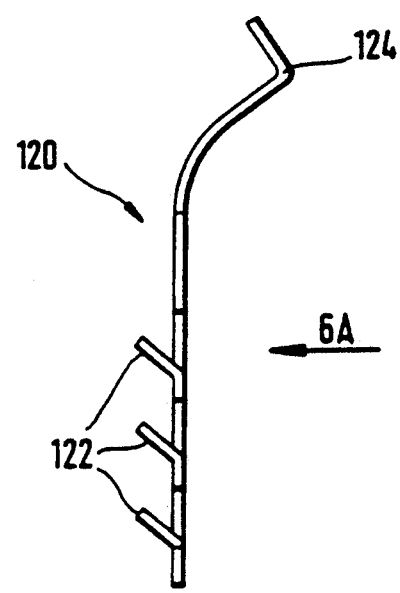

FIGS. 5a to 5e are, respectively, a sectional view, a top and a bottom plan view, and two side elevations of an inner portion associated with the outer portion of the two-part protective cover of FIGS. 4a and 4b; and FIGS. 6a and 6b are various representations of a detent spring for the two-part protective cover of FIGS. 4a and 4b as well as 5a to 5e.

Figure 1A:
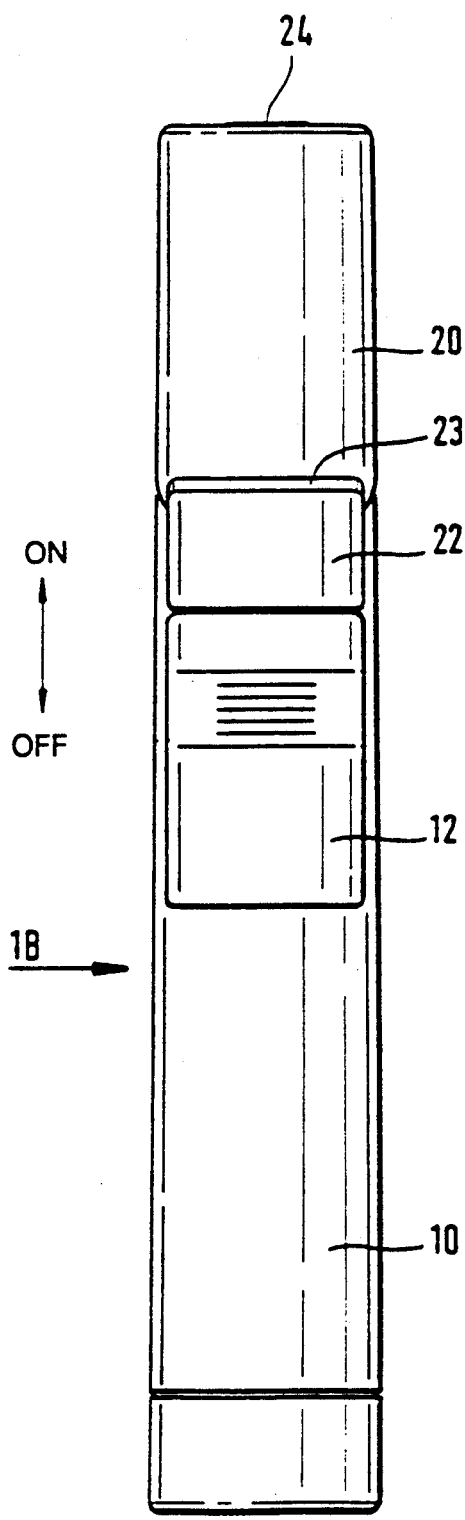
FIGS. 1a and 1b are, respectively, a front elevation and a side elevation of an electric toothbrush showing the protective cover in pushed-on position.
Figure 1B:
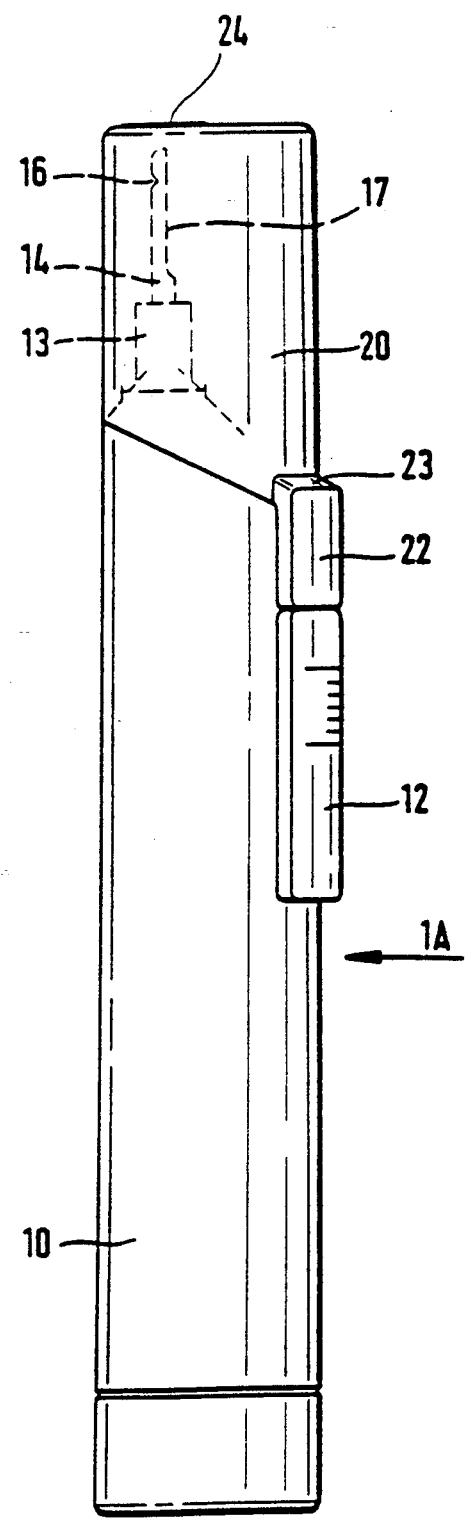

The toothbrush shown in FIGS. 1a and 1b is comprised of a handle section 10 and a protective cover 20. The handle section 10 accommodates an electric motor drive mechanism, accumulators for the supply of energy, as well as the associated electronic control system. Further, the handle section 10 provides a switch 12 for activating and deactivating the electric motor drive mechanism. FIG. 1a shows the toothbrush in a front elevation as seen looking on the switch 12 from the direction A of FIG. 1b, while FIG. 1b shows the toothbrush in a side view as seen looking from the direction B of FIG. 1a.

The handle section 10 is a barrel-shaped, elongated structure of circular cross section. As becomes apparent from FIG. 1b, the handle section 10 has its upper end beveled. At this end, a drive shaft 14 projects from the handle section 10 through a housing shank 13, the drive shaft 14 being arranged off-center, yet parallel to the longitudinal extent of the handle section 10.

The switch 12 is constructed as a slide switch conformed to the shape of the circular cross section of the handle section 10. As indicated in FIG. 1a, the switch 12 has two positions reflecting an On condition and an Off condition of the electric motor drive mechanism. These positions are set by displacing the switch 12 in the longitudinal direction of the handle section 10. As this occurs with the protective cover 20 removed, the switch position reflecting the On state is set by displacing the switch 12 in the direction of the drive shaft 14. The switch position reflecting the Off state of the electric motor drive mechanism is set by shifting the switch 12 in the opposite direction; this position is accordingly provided at the end of the switch 12 remote from the drive shaft 14.

For operation of the electric toothbrush, the protective cover 20 is removed from the handle section 10, and a brush section not shown in FIGS. 1a and 1b is coupled to the housing shank 13 of the handle section 10. For radially securing and locating the brush section, that is, for preventing a rotational movement of the brush section, the housing shank 13 is provided with a cross-sectional profile to which the brush section is suitably conformed. For axially securing and locating the brush section relative to the handle section 10, that is, for preventing a movement of the brush section in the longitudinal direction, the drive shaft 14 is provided with a notch 16 for locking engagement with appropriate means of the brush section. Further, the brush section includes another shaft enabling a bristle supporting structure and thus the bristles to be rotated. This shaft of the brush section is conformed to a flattened surface 17 of the drive shaft 14, thereby allowing transmission of a driving torque from the drive shaft 14 to the shaft of the brush section. This connection between the handle section 10 and such a detachable brush section is described in detail in U.S. patent application Ser. No. 07/855,707, filed May 5, 1992 and assigned to Braun AG referred to in the foregoing, express reference to which is again made.

As already mentioned, in the present case the handle section 10 is not coupled to a brush section. Instead, the protective cover 20 is provided which may be releasably pushed on the handle section 10. The protective cover 20 is cup-shaped, fitting with its open end over the drive shaft 14 for seating engagement with the handle section 10. The protective cover 20 thus encompasses the housing shank 13 and the drive shaft 14 completely. The protective cover 20 is of a circular cross section corresponding to the circular cross section of the handle section 10. In accordance with FIG. 1b, the protective cover 20 further has its open end suitably conformed to the beveled configuration of the upper end of the handle section 10. The protective cover 20 may be further matched with the handle section 10 in respect of color and material, for example, by manufacturing both the handle section 10 and the protective cover 20 of the same plastic material as injection-molded parts.

The protective cover 20 is provided with a safety interlock 22 attached to the open end of the protective cover 20. The safety interlock 22 is constructed as a tongue-shaped component projecting by means of a shoulder 23 beyond the boundaries of the protective cover 20. As becomes apparent from FIGS. 1a and 1b, the safety interlock 22 extends up to the switch 12 on the handle section 10 with the protective cover 20 in pushed-on position. The safety interlock 22 has its shape conformed to the circular cross section of the handle section 10 as well as to the width of the switch 12. The extent of the safety interlock 22 in the longitudinal direction of the handle section 10 is such that it just borders on the switch 12 when the switch is in the position reflecting the Off state of the electric motor drive mechanism. The activation direction of the switch 12 towards the protective cover being predetermined, the opposing safety interlock 22 prevents the switch 12 and thus the electric motor drive from being activated with the protective cover 20 seated in place. In seated position, the protective cover 20 accordingly prevents activation of the electric toothbrush.

To ensure that the protective cover 20 is retained on the handle section 10, the protective cover 20 has in its interior locking means engaging in the notch 16 of the drive shaft 14 when the protective cover 20 is seated to thereby establish a locking engagement. In this manner, the protective cover 20 is secured against axial movement, particularly against disengagement from the handle section 10. It will thus be seen that the notch 16 of the drive shaft 14 not only serves the initially explained function of locating a detachable brush section in axial direction, but also serves at the same time to locate the protective cover on the handle section 10 and secure it thereto.

Finally, the protective cover 20 is provided with drain holes 24 only indicated in FIGS. 1a and 1b and allowing liquids such as water still clinging to the drive shaft 14 to be drained from the protective cover 20.

Figure 2A:
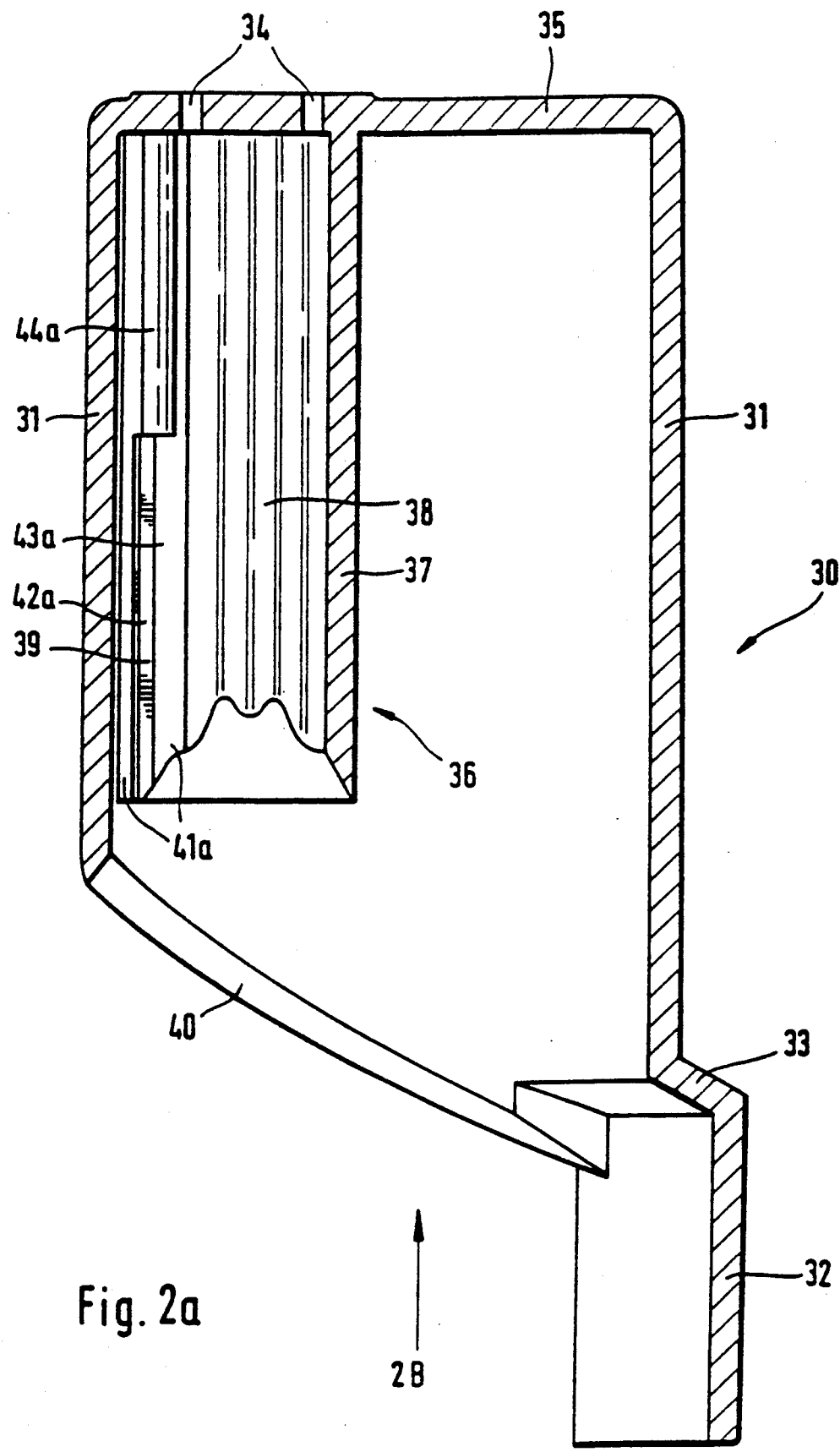
FIGS. 2a and 2b are, respectively, a sectional view of an integrally formed protective cover and a view into the interior of the protective cover.
Figure 2B:
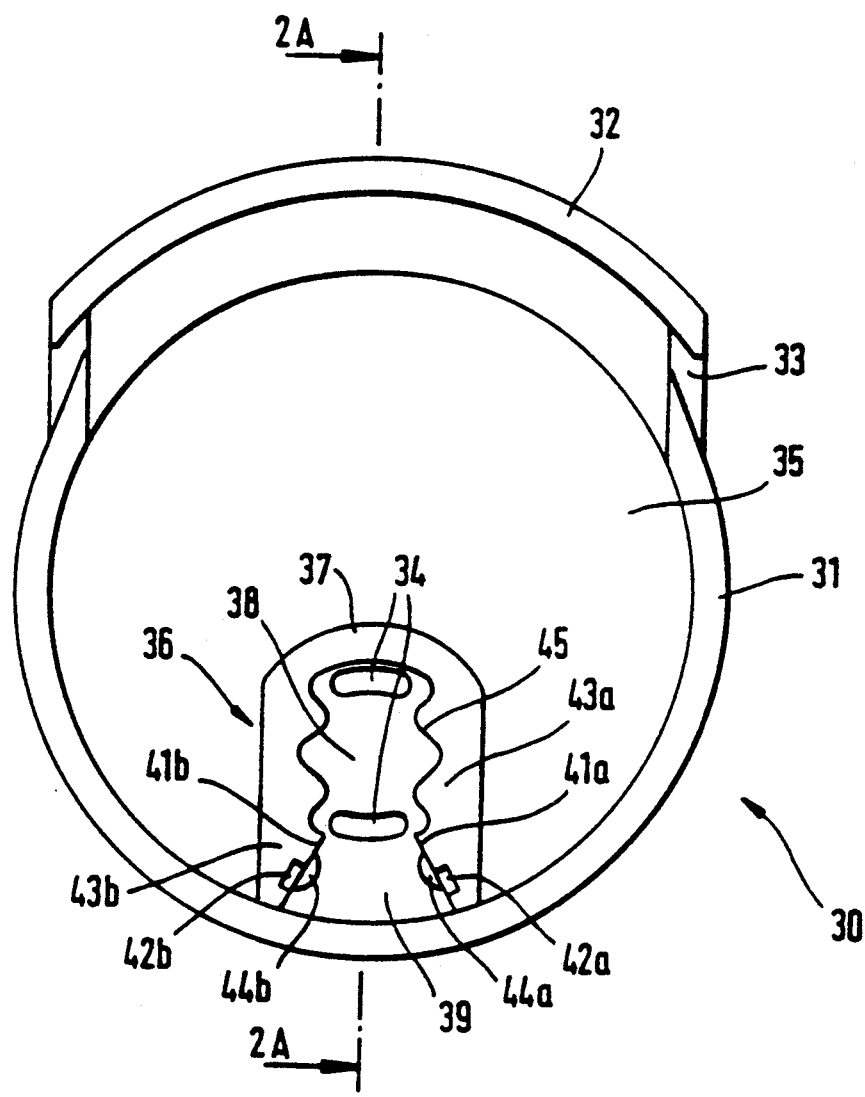

FIGS. 2a and 2b show an integrally formed protective cover 30, whereof FIG. 2a is a sectional view taken along the line A—A of FIG. 2b, and FIG. 2b is a view into the interior of the protective cover 30, as seen looking from the direction B of FIG. 2a.

The protective cover 30 includes a cylindrical outer wall 31 having its upper end closed by a bottom 35. At its lower, open end, the protective cover 30 has a bevel 40 conformed to the bevel of the handle section 10, as already mentioned. The protective cover 30 further has at its lower end a shoulder 33 to which a tongue 32 acting as a safety interlock is attached. The tongue 32 extends beyond the boundaries of the protective cover 30, as shown in FIG. 2a. In accordance with FIG. 2b, the tongue 32 is conformed to the circular cross section of the outer wall 31, extending over about one fourth of the entire periphery.

The interior of the protective cover 30 contains an inner portion 36 which is connected with the bottom 35 and with the left-hand outer wall 31 when viewing FIG. 2a, which outer wall is reduced in length because of the bevel 40, the inner portion having almost the same length as the outer wall 31. The inner portion 36 is provided with recesses 38, 39 arranged in the longitudinal direction and bounded by a wall 37 as well as by end walls 43a, b. The recess 38 extends from the bottom 35 of the protective cover 30 up to the open end of the inner portion 36, while the recess 39 extends from the open end up to abutment stops 44a, b.

In accordance with FIG. 2b, recess 38 has a cross-sectional profile 45 complementary to the cross-sectional profile of the housing shank 13 of the handle section 10 shown in FIG. 1b. As the protective cover 30 is placed down on the handle section 10, the housing shank 13 will enter the recess 38 inside the protective cover 30. The complementary cross-sectional profiles of the housing shank 13 and the recess 38 prevent turning of the protective cover 30 relative to the handle section 10. Two drain holes 34 are provided in the bottom 35 in the area of the recess 38.

The recess 39 serves to receive locking means. In the present case, the locking means is a detent spring 50 which is shown in FIGS. 3a to 3d in various representations and will be described in more detail in the following.

As becomes apparent from FIG. 2b, two grooves 42a, b are provided in the end walls 43a, b. Further, two abutment surfaces 41a, b each are provided adjacent to a respective one of the grooves 42a, b. The grooves 42a, b as well as the abutment surfaces 41a, b are arranged parallel to the recesses 38, 39, that is, in the longitudinal direction. In accordance with FIG. 2a, the grooves 42a, b and the abutment surfaces 41a, b extend only up to the abutment stops 44a, b. In this arrangement, the grooves 42a, b and the abutment surfaces 41a, b serve to receive and guide the detent spring 50.

The detent spring 50 shown in FIGS. 3a to 3d in a variety of representations is comprised of a mid-portion 53 and two guiding surfaces 51a, b adjoining the mid-portion 53. In accordance with FIG. 3c, the guiding surfaces 51a, b are arranged at such an angle to the mid-portion 53 that the mid-portion 53 and the guiding surfaces 51a, b combine to form a roof-shaped structure.

Each of the guiding surfaces 51a, b is provided with two guiding tabs 52a, b projecting from the guiding surfaces 51a, b. At the end of each guiding surface 51a, b a respective claw structure 54a, b is provided protruding from the guiding surface 51a, b in the same direction as the guiding tabs 52a, b.

A locking tab 56 is provided on an extension 55 of the mid-portion 53 at its end of remote from the claws 54a, b. According to FIG. 3a, the locking tab 56 is of a V-shaped cross section, projecting beyond the surface formed by the mid-portion 53 because of an angled configuration of the extension 55. The detent spring 50 is made of stainless spring steel, for example.

The detent spring 50 is inserted into the recess 39 of the protective cover 30 in the manner shown in FIG. 3c in a direction corresponding to the view of FIG. 2b. In the process, the guiding surfaces 51, b come to rest against the abutment surfaces 41a, b, and the guiding tabs 52a, b engage in the grooves 42a, b. The detent spring 50 thus bears against the abutment surfaces 41a, b and is guided by its guiding tabs 52a, b engaging in the grooves 42a, b. It is necessary to introduce the locking tab 56 into the recess 39 first, so that the claws 54a, b do not contact the abutment surfaces 41a, b until the detent spring 50 is completely inserted. Exerting a pressure on the detent spring 50 to insert it farther into the recess 39 causes the claws 54a, b to enter the material of the abutment surfaces 41a, b. In this manner, a stable connection results between the detent spring 50 and the protective cover 30, preventing the detent spring 50 from falling out of the protective cover 30.

With the detent spring 50 inserted, the locking tab 56 extends in the lower area 38, that is, in the proximity of the bottom 35, up to about the center of the recess 38. Seating the protective cover 30 on the handle section 10 causes at the same time the drive shaft 14 to be introduced into the recess 38 and to be received by it. The notch 16 of the drive shaft 14 then becomes operatively associated with the locking tab 56 projecting into the recess 38, such that the locking tab 56 falls into the notch 16. By suitably configuring the detent spring 50, in particular its extension 55, this locking action occurs under spring tension. This provides a safe connection between the pushed-on protective cover 30 and the handle section 10 keeping the protective cover 30 from falling off.

FIGS. 4a and 4b show an outer portion 60 of a two-part protective cover, whereof FIG. 4a is a sectional view taken along the line A—A of FIG. 4b, and FIG. 4b is a view into the interior of the protective cover, as seen looking from the direction B of FIG. 4a.

The protective cover is comprised of a cylindrical outer wall 61 having its upper end closed by a bottom 65. At its open end, the outer portion 60 has a bevel 67 conformed to the bevel of the handle section 10, as already mentioned. The outer portion 60 further has a shoulder 63 providing a tongue 62 acting as a safety interlock and extending beyond the boundaries of the outer portion 60, as shown in FIG. 4a. In accordance with FIG. 4b, the tongue 62 is conformed to the circular cross section of the outer wall 61, extending over about one fourth of the periphery.

Attached to the inside of the tongue 62 is a projection 68 which extends over a middle partial area of the tongue 62 according to FIG. 4b and parallel to the bottom 65 of the outer portion 60 according to FIG. 4a, protruding from the tongue 62 by a small amount. At the bottom 65, a rib member 66 of circular configuration according to FIG. 4b projects in longitudinal direction in the area of the left-hand outer wall 61, when viewing FIG. 4a, which wall is reduced in length because of the bevel 67. In the area enclosed by the rib member 66, a total of four drain holes 64 are provided in the bottom 65.

FIGS. 5a to 5e show an inner portion 80 of the two-part protective cover which is adapted to be connected with the outer portion 60. FIG. 5a is a sectional view taken along the line A—A of FIGS. 5b and 5c, FIG. 5b is a top view into the interior of the inner portion 80 as seen looking from the direction B of FIG. 5a, and FIG. 5c is a bottom view of the inner portion 80 as seen looking from the direction C of FIG. 5a.

The inner portion 80 has a funnel-shaped guided-entry surface 82 formed by a wall 83. As becomes apparent from FIG. 5a and FIG. 5e, this guided-entry surface 82 is formed considering again the bevel of the handle section 10 of FIG. 1b.

According to FIG. 5a, the guided-entry surface 82 continues in recesses 84, 85, 86 formed by walls 87. The arrangement of the recesses 84, 85, 86 is such that they extend parallel to the longitudinal direction with the inner portion 80 and the outer portion 60, that is, the protective cover, assembled. Recess 85 has a cross-sectional profile 89 complementary to the cross-sectional profile of the housing shank 13 of the handle section 10. With the protective cover assembled and pushed on, these cross-sectional profiles are in relative engagement, thereby preventing the possibility of turning of the protective cover on the handle section 10.

Further, in a mid-area of the inner portion 80 the walls 87 are configured such as to provide two projections 98a, b enclosing two grooves 99a, b. The grooves 99a, b are in opposed symmetrical arrangement and interconnected by an abutment surface 100. The grooves 99a, b and the abutment surface 100 serve a guiding and retaining function for locking means. In the present arrangement, a detent spring 120 is provided as a locking means which is illustrated in FIGS. 6a and 6b and will be explained as the description proceeds.

The inner portion 80 has at its upper end a rib member 92 of a semicircular configuration according to FIG. 5a. The upper end of the inner portion 80 further provides a total of three supporting members 94a, b, c which project longitudinally upwardly from the inner portion as the rib member 92. Between the rib member 92 and the supporting members 94a, b, c a respective groove 95a, b, c is provided which is conformed to the rib member 66 of the outer portion 60 in respect of its width transversely to the longitudinal direction and its extent in the longitudinal direction. Further, the outside diameter of the rib member 92 of the inner portion 80 corresponds to the inside diameter of the rib member 66 of the outer portion 60.

At the lower end of the inner portion 80, an edge 88 is provided which is associated with the projection 68 of the outer portion 60 and is therefore situated in the area of the guided-entry surface 82 which is longer because of the bevel. In this area, two drain channels 90a, b are provided as becomes particularly apparent from FIGS. 5d and 5e.

Finally, the inner portion 80 includes two supporting walls 102a, b extending parallel to the recesses 84, 85, 86 and thus in the longitudinal direction. According to FIG. 5b, the supporting walls 102a, b are conformed to the circular cross section of the outer wall 61 of the outer portion 60. The supporting walls 102a, b extend over a certain area in the longitudinal direction, as will be seen in particular from FIGS. 5d and 5e.

To assemble the inner portion 80 and the outer portion 60, the inner portion 80 is introduced into the opening of the outer portion 60 using first the upper end illustrated in FIG. 5a. Because the grooves 95a, b, c of the inner portion 80 are accurately adapted to the rib member 66 of the outer portion 60, the rib member 66 can be inserted into the grooves 95a, b, c identified. The inner portion 80 thus has its upper end clearly located on the bottom 65 of the outer portion 60. The inner portion 80 then has to be turned about its longitudinal axis such that the edge 88 of the inner portion 80 abuts exactly against the projection 68 of the outer portion 60. This will be the case when the respective bevels of the inner portion 80 and of the outer portion 60 are congruent. The edge 88 of the inner portion 80 can then be urged over the projection 68 of the outer portion 60 until its locking engagement on the side of the projection 68 proximate to the shoulder 63. The edge 88 and the projection 68 thus provide a firm connection between the inner portion 80 and the outer portion 60. The projection 68 prevents the inner portion 80 from falling out of the outer portion 60. Moreover, the supporting walls 102a, b which have their outsides in abutment with the insides of the outer wall 61 provide for further stabilization of the inner portion 80 inside the outer portion 60.

The detent spring 120 illustrated in FIGS. 6a and 6b is of an elongated configuration, having on either side three retaining claws 122 protruding from the surface formed by the detent spring 120. In its upper area when viewing FIGS. 6a and 6b, the detent spring 120 is bent into the direction opposite that of the retaining claws 122 and provided with a V-shaped locking tab 124. The detent spring 120 may be made of spring steel.

With its sides and the retaining claws 122 provided thereon, the detent spring 120 is inserted into the grooves 99a, b. As this occurs, the detent spring 120 rests against the abutment surface 100 of the inner portion 80. The retaining claws 122 entering into the material of the projections 98a, b, they establish a stable connection between the detent spring 120 and the inner portion 80. It is necessary for the detent spring 120 to be introduced into the grooves 99a, b such that the locking tab 124 projects into the area of the recess 86 of the inner portion 80. The curvature of the detent spring 120 is configured such that the locking tab 124 lies approximately in the center of the recess 86.

With the detent spring 120 inserted and the inner portion 80 and the outer portion 60 assembled together, seating the protective cover assembly on the handle section 10 causes at the same time the drive shaft 14 to be introduced into the recess 86 in which it is received, as shown in FIG. 1b. As a result, the detent spring 120 becomes operatively associated with the notch 16 of the drive shaft 14, such as to cause locking engagement of the locking tab 124 with the notch 16. This locking engagement occurs under spring tension, because the detent spring 120 is suitably biased. In this manner, a stable connection is accomplished between the two-part protective cover described and the handle section 10. The possibility of the protective cover becoming detached from the handle section 10 is thereby prevented.

Overall, both the integrally formed protective cover and the two-part protective cover described ensure a reliable protection of, in particular, the drive shaft from contaminants, liquids and the impact of forces, in addition to preventing at the same time an accidental operation of the electric toothbrush.

In an advantageous embodiment, the protective cover may be provided with a chamber or a cavity adapted to store one or several toothbrush attachments. Where the cavity is molded into the outer wall of the protective cover, it will be advantageous to provide locking means in the cavity for locating the toothbrush attachment inside the cavity in locking engagement therewith, yet releasably. In a further embodiment, the substantially cylindrical outer wall of the protective cover is comprised of two semicylindrical shells interconnected at one end by means of a film hinge and adapted to be closed by locking engagement and opened at the other end for the purpose of receiving a removable toothbrush attachment in the interior of the protective cover. By this means, the protective cover serves an additional storage function for toothbrush attachments, allowing their storage in a hygienic, safe and easy-to-find manner particularly in a traveler's luggage. It will be understood that also replacement brush heads may be stored in/on the protective cove in lieu of the toothbrush attachment.

I claim:

1. A protective device for an electric toothbrush including a handles section accommodating an electric motor drive mechanism as well as a switch providing at least two switch positions reflecting an On and an Off condition of the electric motor drive mechanism, said protective device comprising a protective cover adapted to be pushed on the handle section and a safety interlock configured such that, with the protective cover pushed on, the switch is prevented from going from the Off position to the On position.

2. The protective device as claimed in claim 1 wherein the handle section and the protective cover are of a barrel-shaped configuration, the switch is actuatable in a longitudinal direction, the switch position reflecting the Off condition being at an end remote from the protective cover when viewed in the longitudinal direction, and, with the protection cover seated in place, the safety interlock extends in the longitudinal direction beyond the boundaries of the protective cover, reaching up to the switch when in the Off position.

3. The protective device as claimed in claim 1 or claim 2 wherein the handles section includes at least one drive shaft connected with the electric motor drive mechanism and provided with at least one notch, and wherein the protective cover further comprises a locking means operatively associated with the notch when the protective cover is seated in place, such as to retain the protective cover in pushed-on condition.

4. The protective device as claimed in claim 3 wherein the notch of the drive shaft serves at the same time a locating function for a brush section.

5. The protective device as claimed in claim 1 wherein the protective cover includes recesses for receiving the drive shaft and a housing shank from which the drive shaft projects, the recesses having at least in part a cross-sectional profile complementary to a cross-sectional profile of the housing shank.

6. The protective device as claimed in claim 5 further comprising a detent spring serving as a locking means and wherein the protective cover has two grooves extending parallel to the recesses and provided to receive the detent spring.

7. The protective device as claimed in claim 6 wherein the detent spring possesses guiding tabs projecting into the grooves of the protective cover when the detent spring is inserted.

8. The protective device as claimed in claim 6 or claim 7 wherein the detent spring includes claw structure preventing the detent spring from falling out when inserted.

9. The protective device as claimed in claim 6 wherein the detent spring includes a locking tab falling into the notch of the drive shaft with the detent spring inserted and the protective cover pushed on.

10. The protective device as claimed in claim 1 wherein the protective cover includes an inner portion and an outer portion provided with a rib member and a projection for holding the inner portion.

11. The protective device as claimed in claim 10 wherein the inner portion includes at least one groove into which the rib member projects with the protective cover assembled, and the inner portion is provided with an edge locking into a space behind the projection in the assembled condition of the protective cover.

12. The protective device as claimed in claim 10 wherein the inner portion includes at least one supporting wall bearing against the outer portion in the assembled condition or the protective cover.

13. The protective device as claimed in claim 10 wherein the inner portion includes recesses for receiving a drive shaft and a housing shank from which the drive shaft projects, the drive shaft and the housing shank being of said handle section, the recesses having at least in part a cross-sectional profile complementary to a cross-sectional profile of the housing shank.

14. The protective device as claimed in claim 13 wherein the inner portion has two grooves which extend parallel to the recesses and are provided to receive a detent spring serving as a locking means.

15. The protective device as claimed in claim 14 wherein the detent spring possesses retaining claws preventing the detent spring from falling out when inserted.

16. The protective device as claimed in claim 14 wherein the detent spring includes a locking tab locking into a notch of the drive shaft with the detent spring inserted and the protective cover assembled and pushed on.

17. The protective device as claimed in claim 13 wherein the inner portion is provided with a funnel-shaped guided-entry surface opening into the recesses and serving to introduce the drive shaft into the recesses when the protective cover is pushed onto the handle section.

18. The protective device as claimed in claim 1 wherein the protective cover is configured in cup shape, surrounding both a drive shaft and a housing shank, both of said handle section.

19. The protective device as claimed in claim 1 wherein the protective cover is made of a plastics material matching with the handle section in respect of form, material, and color.

* * * * *